United States Patent
Marsala

(10) Patent No.: US 11,472,859 B2
(45) Date of Patent: Oct. 18, 2022

(54) METHOD AND COMPOSITION FOR TREATING NEURONAL HYPER-EXCITABTIITY

(71) Applicant: The Regents of the University of California, Oakland, CA (US)

(72) Inventor: Martin Marsala, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 839 days.

(21) Appl. No.: 16/084,912

(22) PCT Filed: Mar. 27, 2017

(86) PCT No.: PCT/US2017/024285
§ 371 (c)(1),
(2) Date: Sep. 13, 2018

(87) PCT Pub. No.: WO2017/172606
PCT Pub. Date: Oct. 5, 2017

(65) Prior Publication Data
US 2019/0071486 A1  Mar. 7, 2019

Related U.S. Application Data

(60) Provisional application No. 62/314,128, filed on Mar. 28, 2016.

(51) Int. Cl.
| | | |
|---|---|---|
| *C07K 14/705* | (2006.01) | |
| *A61K 48/00* | (2006.01) | |
| *C12N 9/88* | (2006.01) | |
| *A61P 25/14* | (2006.01) | |
| *C07C 235/42* | (2006.01) | |
| *C07C 233/69* | (2006.01) | |
| *C07C 235/34* | (2006.01) | |

(52) U.S. Cl.
CPC ...... *C07K 14/70571* (2013.01); *A61K 48/005* (2013.01); *A61K 48/0075* (2013.01); *A61P 25/14* (2018.01); *C07C 233/69* (2013.01); *C07C 235/34* (2013.01); *C07C 235/42* (2013.01); *C12N 9/88* (2013.01); *C12Y 401/01015* (2013.01); *C12N 2710/00* (2013.01); *C12N 2750/14143* (2013.01)

(58) Field of Classification Search
CPC .... C12N 15/86; C12N 15/861; C12N 15/867; C12Y 401/01015
See application file for complete search history.

(56) References Cited

U.S. PATENT DOCUMENTS

| | | |
|---|---|---|
| 5,871,487 A | 2/1999 | Warner et al. |
| 8,292,874 B2 | 10/2012 | Stivland et al. |
| 9,827,109 B2 | 11/2017 | Steinberg |
| 10,688,285 B2 | 6/2020 | Marsala et al. |
| 2002/0082390 A1 | 6/2002 | Friddle et al. |
| 2003/0130577 A1 | 7/2003 | Purdy et al. |
| 2008/0051357 A1 | 2/2008 | Chang et al. |
| 2010/0030184 A1 | 2/2010 | Boulis et al. |
| 2012/0221063 A1 | 8/2012 | Abdou |
| 2013/0211380 A1 | 8/2013 | Aquino et al. |
| 2014/0058357 A1 | 2/2014 | Keyser et al. |
| 2014/0073684 A1 | 3/2014 | Stoffel et al. |
| 2015/0224331 A1 | 8/2015 | Marsala |
| 2015/0343038 A1 | 12/2015 | Marsala |
| 2016/0081956 A1 | 3/2016 | Kaufman et al. |
| 2017/0151416 A1* | 6/2017 | Kutikov ................ A61K 38/18 |
| 2018/0008727 A1 | 1/2018 | Marsala |
| 2018/0117282 A1 | 5/2018 | Marsala et al. |

FOREIGN PATENT DOCUMENTS

| | | |
|---|---|---|
| CN | 101528922 A | 9/2009 |
| CN | 103328038 A | 9/2013 |
| WO | 1994/10988 A | 5/1994 |
| WO | 2004/060464 A2 | 7/2004 |
| WO | 2010/071832 A1 | 6/2010 |
| WO | 2011/057171 A1 | 5/2011 |
| WO | 2012/075337 A2 | 6/2012 |
| WO | 2014/047540 A1 | 3/2014 |
| WO | 2014/116652 A2 | 7/2014 |
| WO | 2014/184576 A2 | 11/2014 |
| WO | 2016/122791 A1 | 8/2016 |
| WO | 2017/172606 A1 | 10/2017 |

OTHER PUBLICATIONS

EP17776384.4 Extended European Search Report dated Jul. 31, 2019.
Kakinohana et al. "Combinational Spinal GAD65 Gene Delivery and Systemic GABA-Mimetic Treatment for Modulation of Spasticity," PLoS One, Jan. 2012, 7(1):e30561.
Kitzman, Patrick. "Changes in vesicular glutamate transporter 2, vesicular GABA transporter and vesicular acetylcholine transporter labeling of sacrocaudal motoneurons in the spastic rat," Experimental Neurology, 2006, 197:407-419.
PCT/US2017/024285 International Search Report and Written Opinion dated Aug. 10, 2017.
Jin et al. "Demonstration of Functional Coupling between Gamma-Aminobutyric acid (GABA) Synthesis and Vesicular GABA Transport into Synaptic Vesicles," Proc Natl Acad Sci USA, Apr. 2003, 100(7):4293-4298.
PCT/US2020/013059 International Search Report and Written Opinion dated Apr. 1, 2020.
Poston et al. "Catheter delivery systems for infusions into the cortex," Journal of Medical Engineering & Technology, Jul. 2011, 35(5):246-253.

(Continued)

*Primary Examiner* — Antonio Galisteo Gonzalez
(74) *Attorney, Agent, or Firm* — Foley & Lardner LLP

(57) ABSTRACT

The present invention provides a therapy for treating loss of GABA-mediated pre-synaptic inhibition after spinal injury. The therapeutic regimen includes spinal segment-specific upregulation of GAD65 (glutamate decarboxylase) and VGAT (vesicular GABA transporter) to modulate chronic spasticity in patients after spinal traumatic or ischemic injury.

20 Claims, 5 Drawing Sheets
Specification includes a Sequence Listing.

(56) References Cited

OTHER PUBLICATIONS

Kantor et al. "Clinical Applications Involving CNS Gene Transfer," Adv Genet., 2014, 87:71-124.
Bouard et al. "Viral vectors: from virology to transgene expression," British Journal of Pharmacology, 2009, 157:153-165.
Adkins et al. "Tiagabine: A Review of its Pharmacodynamic and Pharmacokinetic Properties and Therapeutic Potential in the Management of Epilepsy," Drugs, Mar. 1998, 55(3):437-460.
Gholizadeh et al. "Transduction of the Central Nervous System After Intracerebroventricular Injection of Adeno-Associated Viral Vectors in Neonatal and Juvenile Mice," Human Gene Therapy Methods, Aug. 2013,24:205-213.
EP14742941 Extended European Search Report dated Jun. 20, 2016.
Dayton et al. "The advent of AAV9 expands applications for brain and spinal cord gene delivery," Expert Opinion on Biological Therapy, Jun. 15, 2012, 12(6):757-766.
Federici et al. "Robust spinal motor neuron transduction following intrathecal delivery of AAV9 in pigs," Gene Therapy, 2012, 19(8):852-859.
Foust et al. "Intravascular AAV9 preferentially targets neonatal neurons and adult astrocytes," Nature Biotechnology, Jan. 2009, 27(1):59-65.
Hirai et al. "Intrathecal shRNA-AAV9 Inhibits Target Protein Expression in the Spinal Cord and Dorsal Root Ganglia of Adult Mice," Human Gene Therapy Methods, Apr. 1, 2012, 23(2):119-127.
EP15880645 Extended European Search Report dated May 24, 2018.
Colak et al. "Adenovirus-mediated gene therapy for experimental spinal cord tumors: tumoricidal efficacy and functional outcome," Brain Research, May 1995, 691:76-82.
JP2017-540569 Office Action dated Jun. 26, 2018.
PCT/US2015/065704 International Search Report dated Feb. 25, 2016.
CN201 580078566.9 Office Action dated Sep. 24, 2019.
JP2017-540569 Office Action dated Jun. 4, 2019.
Bell et al. "Motor Neuron Transduction After Intracisternal Delivery of AAV9 in a Cynomolgus Macaque," Human Gene Therapy Methods, Apr. 2015, 26:43-44.
Duque et al. "Intravenous Administration of Self-complementary AAV9 Enables Transgene Delivery to Adult Motor Neurons," Molecular Therapy, Jul. 2009, 17(7):1187-1196.
Foust et al. "Therapeutic AAV9-mediated Suppression of Mutant SOD1 Slows Disease Progression and Extends Survival in Models of Inherited ALS," Molecular Therapy, Dec. 2013, 21(12):2148-2159.
Gray et al. "Preclinical Differences of Intravascular AAV9 Delivery to Neurons and Glia: A Comparative Study of Adult Mice and Nonhuman Primates," Molecular Therapy, Jun. 2011, 19(6):1058-1069.
Kakinojana et al. "Region-specific cell grafting into cervical and lumbar spinal cord in rat: a qualitative and quantitative stereological study," Experimental Neurology, 2004, 190:122-132.
Meyer et al. "Improving Single Injection CSF Delivery of AAV9-mediated Gene Therapy for SMA: A Dose-response Study in Mice and Nonhuman Primates," Molecular Therapy, Mar. 2015, 23(3):477-487.
Passini et al. "Translational Fidelity of Intrathecal Delivery of Self-Complementary AAV9-Survival Motor Neuron 1 for Spinal Muscular Atrophy," Human Gene Therapy, Jul. 2014, 25:619-630.
Usvald et al. "Analysis of Dosing Regimen and Reproducibility of Intraspinal Grafting of Human Spinal Stem Cells in Immunosuppressed Minipigs," Cell Transplantation, 2010, 19:1103-1122.
Xiao et al. "Production of High-Titer Recombinant Adeno-Associated Virus Vectors in the Absence of Helper Adenovirus," Journal of Virology, Mar. 1998, 72(3):2224-2232.
Xu et al. In Vivo Gene Knockdown in Rat Dorsal Root Ganglia Mediated by Self-Complementary Adeno-Associated Virus Serotype 5 Following Intrathecal Delivery, PLoS One, Mar. 2012, 7(3):e32581.
CN201580078566.9 Office Action dated Apr. 28, 2020.
Bu et al. "Two human glutamate decarboxylases, 65-kDa GAD and 67-kDa GAD, are each encoded by a single gene," Proc. Natl. Acad. Sci. USA, Mar. 1992, 89:2115-2119.
Chaudhry et al. "The Vesicular GABA Transporter, VGAT, Localizes to Synaptic Vesicles in Sets of Glycinergic as Well as GABAergic Neurons," The Journal of Neuroscience, Dec. 1, 1998, 18(23):9733-9750.

\* cited by examiner

Quantitative analysis of GAD65 and VGAT expression.

| Lumbar Subpial AAV9 delivery | GAD65 | VGAT | VGLUT1 + GAD65 | VGLUT1 + VGAT | VGLUT2+ GAD65 | VGLUT2+ VGAT |
|---|---|---|---|---|---|---|
| Experimental Groups | % Normalized Signal (Integrated Density) | | Co-expressing Puncta (* P<0.01) | | | |
| AAV9-GAD65/VGAT (n=4; 6 sections/animal) | 208±19* | 166±25* | 14±8* | 9±3.4* | 245±97* | 331±67* |
| AAV9-GFP (n=4; 6 sections/animal) | 100±7 | 100±15 | 2±1 | 2±0.9 | 1±0.7 | 5±1 |

SEQUENCE LISTING

```
<160> NUMBER OF SEQ ID NOS: 4

<210> SEQ ID NO 1
<211> LENGTH: 585
<212> TYPE: PRT
<213> ORGANISM: Homo sapiens

<400> SEQUENCE: 1

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160
```

```
Met His Cys Gln Thr Thr Leu Lys Tyr Ala Ile Lys Thr Gly His Pro
            165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
            195                 200                 205

Ile Ala Pro Val Phe Val Leu Leu Glu Tyr Val Thr Leu Lys Lys Met
210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
            245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
            275                 280                 285

Ala Ala Ala Leu Gly Ile Gly Thr Asp Ser Val Ile Leu Ile Lys Cys
            290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
            325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
            355                 360                 365

Gly Gly Leu Leu Met Ser Arg Lys His Lys Trp Lys Leu Ser Gly Val
            370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
            405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
            435                 440                 445

His Val Asp Val Phe Lys Leu Trp Leu Met Trp Arg Ala Lys Gly Thr
450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
            485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
            515                 520                 525

Val Ala Pro Val Ile Lys Ala Arg Met Met Glu Tyr Gly Thr Thr Met
530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
            565                 570                 575
```

Glu Ile Glu Arg Leu Gly Gln Asp Leu
          580                 585

<210> SEQ ID NO 2
<211> LENGTH: 1803
<212> TYPE: DNA
<213> ORGANISM: Homo sapiens

<400> SEQUENCE: 2

| | | | | | |
|---|---|---|---|---|---|
| atgtcccta | tacatcacca | tcaccatcac | ctggttccgc | gtggatccga | agcttcgaat | 60 |
| tctggctttt | ggtctttcgg | gtcggaagat | ggctctgggg | attccgagaa | tcccggcaca | 120 |
| gcgcgagcct | ggtgccaagt | ggctcagaag | ttcacgggcg | gcatcggaaa | caaactgtgc | 180 |
| gccctgctct | acggagacgc | cgagaagccg | gcggagagcg | gcgggagcca | accccgcgg | 240 |
| gccgccgccc | ggaaggccgc | ctgcgcctgc | gaccagaagc | cctgcagctg | ctccaaagtg | 300 |
| gatgtcaact | acgcgtttct | ccatgcaaca | gacctgctgc | cggcgtgtga | tggagaaagg | 360 |
| cccactttgg | cgtttctgca | agatgttatg | aacattttac | ttcagtatgt | ggtgaaaagt | 420 |
| ttcgatagat | caaccaaagt | gattgatttc | cattatccta | atgagcttct | ccaagaatat | 480 |
| aattgggaat | tggcagacca | accacaaaat | tggaggaaa | ttttgatgca | ttgccaaaca | 540 |
| actctaaaat | atgcaattaa | aacagggcat | cctagatact | tcaatcaact | ttctactggt | 600 |
| ttggatatgg | ttggattagc | agcagactgg | ctgacatcaa | cagcaaatac | taacatgttc | 660 |
| acctatgaaa | ttgctccagt | atttgtgctt | ttggaatatg | tcacactaaa | gaaaatgaga | 720 |
| gaaatcattg | ctggccagg | gggctctggc | gatgggatat | tttctcccgg | tggcgccata | 780 |
| tctaacatgt | atgccatgat | gatcgcacgc | tttaagatgt | tcccagaagt | caaggagaaa | 840 |
| ggaatggctg | ctcttcccag | gctcattgcc | ttcacgtctg | aacatagtca | tttttctctc | 900 |
| aagaagggag | ctgcagcctt | aggattgga | acagacagcg | tgattctgat | taaatgtgat | 960 |
| gagagaggga | aaatgattcc | atctgatctt | gaaagaagga | ttcttgaagc | caaacagaaa | 1020 |
| gggtttgttc | ctttcctcgt | gagtgccaca | gctggaacca | ccgtgtacgg | agcatttgac | 1080 |
| cccctcttag | ctgtcgctga | catttgcaaa | aagtataaga | tctggatgca | tgtggatgca | 1140 |
| gcttggggtg | ggggattact | gatgtcccga | aaacacaagt | ggaaactgag | tggcgtggag | 1200 |
| agggccaact | ctgtgacgtg | gaatccacac | aagatgatgg | gagtccctt | gcagtgctct | 1260 |
| gctctcctgg | ttagagaaga | gggattgatg | cagaattgca | accaaatgca | tgcctcctac | 1320 |
| ctctttcagc | aagataaaca | ttatgacctg | tcctatgaca | ctggagacaa | ggccttacag | 1380 |
| tgcggacgcc | acgttgatgt | ttttaaacta | tggctgatgt | ggagggcaaa | ggggactacc | 1440 |
| gggtttgaag | cgcatgttga | taatgtttg | gagttggcag | agtatttata | caacatcata | 1500 |
| aaaaaccgag | aaggatatga | gatggtgttt | gatgggaagc | ctcagcacac | aaatgtctgc | 1560 |
| ttctggtaca | ttcctccaag | cttgcgtact | ctggaagaca | atgaagagag | aatgagtcgc | 1620 |
| ctctcgaagg | tggctccagt | gattaaagcc | agaatgatgg | agtatggaac | cacaatggtc | 1680 |
| agctaccaac | ccttgggaga | caaggtcaat | ttcttccgca | tggtcatctc | aaacccagcg | 1740 |
| gcaactcacc | aagacattga | cttcctgatt | gaagaaatag | aacgccttgg | acaagattta | 1800 |
| taa | | | | | | 1803 |

<210> SEQ ID NO 3
<211> LENGTH: 525
<212> TYPE: PRT
<213> ORGANISM: Homo sapiens

```
<400> SEQUENCE: 3

Met Ala Thr Leu Leu Arg Ser Lys Leu Ser Asn Val Ala Thr Ser Val
1               5                   10                  15

Ser Asn Lys Ser Gln Ala Lys Met Ser Gly Met Phe Ala Arg Met Gly
            20                  25                  30

Phe Gln Ala Ala Thr Asp Glu Glu Ala Val Gly Phe Ala His Cys Asp
        35                  40                  45

Asp Leu Asp Phe Glu His Arg Gln Gly Leu Gln Met Asp Ile Leu Lys
    50                  55                  60

Ala Glu Gly Glu Pro Cys Gly Asp Glu Gly Ala Glu Ala Pro Val Glu
65              70                  75                  80

Gly Asp Ile His Tyr Gln Arg Gly Ser Gly Ala Pro Leu Pro Pro Ser
                85                  90                  95

Gly Ser Lys Asp Gln Val Gly Gly Gly Glu Phe Gly Gly His Asp
            100                 105                 110

Lys Pro Lys Ile Thr Ala Trp Glu Ala Gly Trp Asn Val Thr Asn Ala
            115                 120                 125

Ile Gln Gly Met Phe Val Leu Gly Leu Pro Tyr Ala Ile Leu His Gly
    130                 135                 140

Gly Tyr Leu Gly Leu Phe Leu Ile Ile Phe Ala Ala Val Val Cys Cys
145                 150                 155                 160

Tyr Thr Gly Lys Ile Leu Ile Ala Cys Leu Tyr Glu Glu Asn Glu Asp
                165                 170                 175

Gly Glu Val Val Arg Val Arg Asp Ser Tyr Val Ala Ile Ala Asn Ala
            180                 185                 190

Cys Cys Ala Pro Arg Phe Pro Thr Leu Gly Gly Arg Val Val Asn Val
    195                 200                 205

Ala Gln Ile Ile Glu Leu Val Met Thr Cys Ile Leu Tyr Val Val Val
210                 215                 220

Ser Gly Asn Leu Met Tyr Asn Ser Phe Pro Gly Leu Pro Val Ser Gln
225                 230                 235                 240

Lys Ser Trp Ser Ile Ile Ala Thr Ala Val Leu Leu Pro Cys Ala Phe
            245                 250                 255

Leu Lys Asn Leu Lys Ala Val Ser Lys Phe Ser Leu Leu Cys Thr Leu
            260                 265                 270

Ala His Phe Val Ile Asn Ile Leu Val Ile Ala Tyr Cys Leu Ser Arg
        275                 280                 285

Ala Arg Asp Trp Ala Trp Glu Lys Val Lys Phe Tyr Ile Asp Val Lys
    290                 295                 300

Lys Phe Pro Ile Ser Ile Gly Ile Ile Val Phe Ser Tyr Thr Ser Gln
305                 310                 315                 320

Ile Phe Leu Pro Ser Leu Glu Gly Asn Met Gln Gln Pro Ser Glu Phe
                325                 330                 335

His Cys Met Met Asn Trp Thr His Ile Ala Ala Cys Val Leu Lys Gly
            340                 345                 350

Leu Phe Ala Leu Val Ala Tyr Leu Thr Trp Ala Asp Glu Thr Lys Glu
        355                 360                 365

Val Ile Thr Asp Asn Leu Pro Gly Ser Ile Arg Ala Val Val Asn Ile
    370                 375                 380

Phe Leu Val Ala Lys Ala Leu Leu Ser Tyr Pro Leu Pro Phe Phe Ala
385                 390                 395                 400

Ala Val Glu Val Leu Glu Lys Ser Leu Phe Gln Glu Gly Ser Arg Ala
                405                 410                 415
```

```
Phe Phe Pro Ala Cys Tyr Ser Gly Asp Gly Arg Leu Lys Ser Trp Gly
            420                 425                 430
Leu Thr Leu Arg Cys Ala Leu Val Val Phe Thr Leu Met Ala Ile
        435                 440                 445
Tyr Val Pro His Phe Ala Leu Leu Met Gly Leu Thr Gly Ser Leu Thr
    450                 455                 460
Gly Ala Gly Leu Cys Phe Leu Leu Pro Ser Leu Phe His Leu Arg Leu
465                 470                 475                 480
Leu Trp Arg Lys Leu Leu Trp His Gln Val Phe Asp Val Ala Ile
            485                 490                 495
Phe Val Ile Gly Gly Ile Cys Ser Val Ser Gly Phe Val His Ser Leu
            500                 505                 510
Glu Gly Leu Ile Glu Ala Tyr Arg Thr Asn Ala Glu Asp
            515                 520                 525

<210> SEQ ID NO 4
<211> LENGTH: 2581
<212> TYPE: DNA
<213> ORGANISM: Homo sapiens

<400> SEQUENCE: 4
gctcgcgccc cgcggcagct ccgcagtgca ctagccacca ccgccgccgc cgccgctccg      60
ccagacctgc tgccagcttg cccggtccag ccctgagaga gcctcgaacg ccagctgcga     120
gggtcatgag ccagagagcc ccggggcgcc gcgcggagag caagcggaga tagcgacttt     180
cgcccccca gccctcgcct tcttgcatcg cgttccccgc atcctcgggt ccttctgtcc     240
tttccgctgt ccccaccgcc gccatggcca ccttgctccg cagcaagctg tccaacgtgg     300
ccacgtccgt gtccaacaag tcccaggcca agatgagcgg catgttcgcc aggatgggtt     360
tcaggcggc cacggatgag gaggcggtgg gcttcgcgca ttgcgacgac ctcgactttg     420
agcaccgcca gggcctgcag atggacatcc tgaaagccga gggagagccc tgcggggacg     480
agggcgctga agcgcccgtc gagggagaca tccattatca gcgaggcagc ggagctcctc     540
tgccgccctc cggctccaag gaccaggtgg aggtggtgg cgaattcggg ggccacgaca     600
agcccaaaat cacggcgtgg gaggcaggct ggaacgtgac caacgccatc cagggcatgt     660
tcgtgctggg cctaccctac gccatcctgc acgcggcta cctggggttg tttctcatca     720
tcttcgccgc cgttgtgtgc tgctacaccg gcaagatcct catcgcgtgc ctgtacgagg     780
agaatgaaga cggcgaggtg gtgcgcgtgc gggactcgta cgtggccata gccaacgcct     840
gctgcgcccc gcgcttccca acgctgggcg ccgagtggt gaacgtagcg cagatcatcg     900
agctggtgat gacgtgcatc ctgtacgtgg tggtgagtgg caacctcatg tacaacagct     960
tcccgggget gcccgtgtcg cagaagtcct ggtccattat cgccacggcc gtgctgctgc    1020
cttgcgcctt ccttaagaac ctcaaggccg tgtccaagtt cagtctgctg tgcactctgg    1080
cccacttcgt catcaatatc ctggtcatag cctactgtct atcgcgggcg cgcgactggg    1140
cctgggagaa ggtcaagttc tacatcgacg tcaagaagtt ccccatctcc attggcatca    1200
tcgtgttcag ctacacgtct cagatcttcc tgccttcgct ggagggcaat atgcagcagc    1260
ccagcgagtt ccactgcatg atgaactgga cgcacatcgc agcctgcgtg ctcaagggcc    1320
tcttcgcgct cgtcgcctac ctcacctggg ccgacgagac caaggaggtc atcacggata    1380
acctgccgg ctccatccgc gccgtggtca acatctttct ggtggccaag cgctgttgt    1440
cctatcctct gccattcttt gccgctgtcg aggtgctgga gaagtcgctc ttccaggaag    1500
```

```
gcagccgcgc cttttccccg gcctgctaca gcggcgacgg gcgcctgaag tcctgggggc    1560
tgacgctgcg ctgcgcgctc gtcgtcttca cgctgctcat ggccatttat gtgccgcact    1620
tcgcgctgct catgggcctc accggcagcc tcacgggcgc cggcctctgt ttcttgctgc    1680
ccagcctctt tcacctgcgc ctgctctggc gcaagctgct gtggcaccaa gtcttcttcg    1740
acgtcgccat cttcgtcatc ggcggcatct gcagcgtgtc cggcttcgtg cactccctcg    1800
agggcctcat cgaagcctac cgaaccaacg cggaggacta gggcgcaagg gcgagccccc    1860
gccgcgcttc tgcgctctct cccttctccc ctcacccgc ccccaccagc ccagtgcgcc    1920
ctgccgccgc gcttgggagg ccaagcttta aacatctctg gttcctagtt tctgattatt    1980
cggggatggg gggatggga gggacaggg attcacgatc catcgcgtct gcgtttctgt      2040
tgtcctttct tttccacaac accctggttt tgggggagg cggggtgcat ttgcgggcag    2100
ggttctctgt ccttccaagt ggggccccga cactttggtt ccagtcatcg aggggggttgg   2160 gaagggaggg agagggggcg cagctcgcag gcgtggcaac ttgaccttgg gggaatattt    2220
cacatccatc cagagctcgg aatctacagc gtccagccat ttccagcaag agcgcttccc    2280
attccggaga cgtttcaacc ctgcagcggg aaaggctgac tgggaaatcc attttgggtg    2340
ggcaatttcc ttcaacgaag ccggaaggcg agaagccgcg gcggggccag cttgcctgcc    2400
ggttttcagg aatctaaact ctcatcttgt gcaatttatc aggtgtggaa ctgttctact    2460
gtgcgtgtgg tgtgctcgtg gtgaataaga tgaaatgtat atcagaaaaa aatctatctc    2520
taatttagag tgcggtacat aattatatcc gcaaataaag aagagacaaa ggctaaaaaa    2580
a                                                                   2581
```

METHOD AND COMPOSITION FOR TREATING NEURONAL HYPER-EXCITABTIITY

CROSS-REFERENCE TO RELATED APPLICATIONS

This application is a US national phase application under 35 USC § 371 of international patent application no. PCT/US2017/024285, filed Mar. 27, 2017, which claims the benefit of priority under 35 U.S.C. § 119(e) of U.S. Ser. No. 62/314,128, filed on Mar. 28, 2016, the entire content of each of which is herein incorporated by reference.

GRANT INFORMATION

This invention was made with Government support under Grant No. NS051644 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Mar. 31, 2017, is named "20378-201384_SL.txt" and is 15,873 bytes in size.

BACKGROUND OF THE INVENTION

Field of the Invention

The invention relates generally to treating spinal injury and more specifically to a combined therapeutic regimen to modulate chronic spasticity in patients after spinal traumatic or ischemic injury.

Background Information

Spinal cord injury (traumatic or ischemic) may lead to the development of clinically-defined spasticity and rigidity. One of the underlying mechanisms leading to the appearance of spasticity after spinal injury is believed to be the loss of local segmental inhibition and the resulting: i) increase in tonic motoneuron firing, ii) increase in primary afferent input during muscle stretch, and/or iii) exacerbated responses to peripheral sensory stimulation (i.e., allodynia). Loss of gamma-aminobutryic acid (GABA)-mediated pre-synaptic, recurrent and reciprocal postsynaptic inhibition as well as the loss of its inhibitory effect in flexor afferent pathways has been shown to represent one of the key mechanisms.

Interestingly, however, previous studies have shown a significant increase in spinal parenchymal GAD67 expression in lumbar spinal segments in Th12 transected cats. Similarly, an increased density of inhibitory boutons apposing α-motoneuron membranes has been shown in adult rats with midthoracic spinal cord transection performed at post-natal day 5. These data suggest that a static increase in GABA synthesizing enzymes in spinal interneurons or increase in the number of inhibitory contacts with α-motoneurons after spinal trauma, in the absence of a specific inhibitory neuron-driven activity, is not sufficient to prevent the development of spasticity/hyperreflexia. In addition to the role of decreased inhibition, several other potential mechanisms have been shown to contribute to the development of spasticity after spinal trauma, including: i) progressive increase in α-motoneuronal 5-$HT_{2C}$ receptor activity which became spontaneously active in the absence of brain-derived serotonin, or ii) the down regulation of the potassium-chloride co-transporter KCC2 in motoneurons and resulting switch to GABA-mediated depolarization. Jointly, these data indicate that the mechanism leading to the development of spasticity after spinal injury (traumatic or ischemic) is complex and can vary depending on the model used as well as the age of experimental animals when the injury is induced.

Clinical pharmacological-treatment studies show that the use of systemic or spinally-administered baclofen ($GABA_B$ receptor agonist) represents the most potent anti-spasticity pharmacological treatment. While effective in modulating spasticity of different etiologies including spinal trauma, amyotrophic lateral sclerosis or central stroke, major side effects such as general sedation and progressive tolerance development often limit its chronic use. The use of systemically-administered GABA-mimetic compounds such as tiagabine (GABA reuptake inhibitor) shows only a weak or no anti-spasticity effect in clinically-acceptable doses, which correlates with a relatively modest potentiation of brain or spinal parenchymal GABA release after systemic delivery. In addition, currently available spinal drug delivery systems (such as epidural or intrathecal delivery) do not permit a spinal segment-restricted therapeutic effect. Because the origin of spasticity affecting individual muscle groups can be somatotopically mapped to specific spinal segments, the development of segment-targeted anti-spasticity treatments would represent a clear advantage over current therapeutic approaches by reducing unwanted side effects. Accordingly, there is a need for novel antispasticity treatments.

SUMMARY OF THE INVENTION

The present invention is based on the observation that a combined treatment composed of spinal segment-specific upregulation of GAD65 (glutamatedecarboxylase) and VGAT (vesicular GABA transporter) in rats with ischemia-induced spasticity leads to an antispasticity effect, and that such a combined treatment results in decreased muscle spasticity.

Accordingly, the invention provides a method of treating spasticity in a subject. The method includes upregulation of GAD65 (glutamate decarboxylase) gene and VGAT (vesicular GABA transporter) gene, thereby treating spasticity in the subject. Upregulation of the GAD65 gene and VGAT gene may be spinal-specific upregulation of the GAD65 gene and VGAT gene, by administering to the subject a viral vector comprising a polynucleotide encoding GAD65 and VGAT, wherein GAD65 and VGAT are expressed, thereby decreasing spasticity. The GAD65 gene and VGAT gene may be overexpressed. The vector may be a lentiviral vector, adenoviral vector, or an adeno-associated vector (AAV). The AAV may be AAV type 9 (AAV9). In various embodiments, the viral vector is administered directly into the spinal parenchyma of the subject, into the intrathecal space of the subject, into the spinal subpial space of the subject, or into a peripheral spastic muscle of the subject.

In another aspect, the invention provides a method of treating spasticity in a subject. The method includes administering to a subject in need thereof a therapeutically effective amount of a viral vector comprising a polynucleotide encoding GAD65 gene and VGAT gene, thereby treating spasticity in the subject. The vector may be a lentiviral vector, adenoviral vector, or an adeno-associated vector (AAV), and may be administered directly into the spine of the subject. The AAV may be AAV type 9 (AAV9). In various embodiments, the vector is administered directly into the spinal parenchyma of the subject, into the intrathecal space of the subject, into the spinal subpial space of the subject, or into a peripheral spastic muscle of the subject.

In another aspect, the invention provides a treatment regimen for treating a subject having a spinal cord injury. The treatment regimen includes administering a viral vector comprising a polynucleotide encoding GAD65 and VGAT, wherein GAD65 and VGAT are expressed, thereby decreasing spasticity. Upregulation of GAD65 and VGAT includes administering a viral vector encoding GAD65 and VGAT, wherein GAD65 and VGAT are expressed and decrease spasticity. The vector may be a lentiviral vector, adenoviral vector, or an adeno-associated vector, and may be administered directly into the spinal parenchyma of the subject, into the intrathecal space of the subject, into the spinal subpial space of the subject, or into a peripheral spastic muscle of the subject. In various embodiments, the vector is administered directly into the spinal parenchyma of the subject, into the intrathecal space of the subject, into the spinal subpial space of the subject, or into a peripheral spastic muscle of the subject.

In another aspect, the present invention provides an expression cassette comprising a promoter or regulatory sequence functionally linked to a polynucleotide encoding GAD65 and VGAT. Also provided are a vector, such as an AAV9, that includes a regulatory sequence such as a promoter functionally linked to a polynucleotide encoding GAD65 and VGAT.

DETAILED DESCRIPTION OF THE INVENTION

Figure 1:
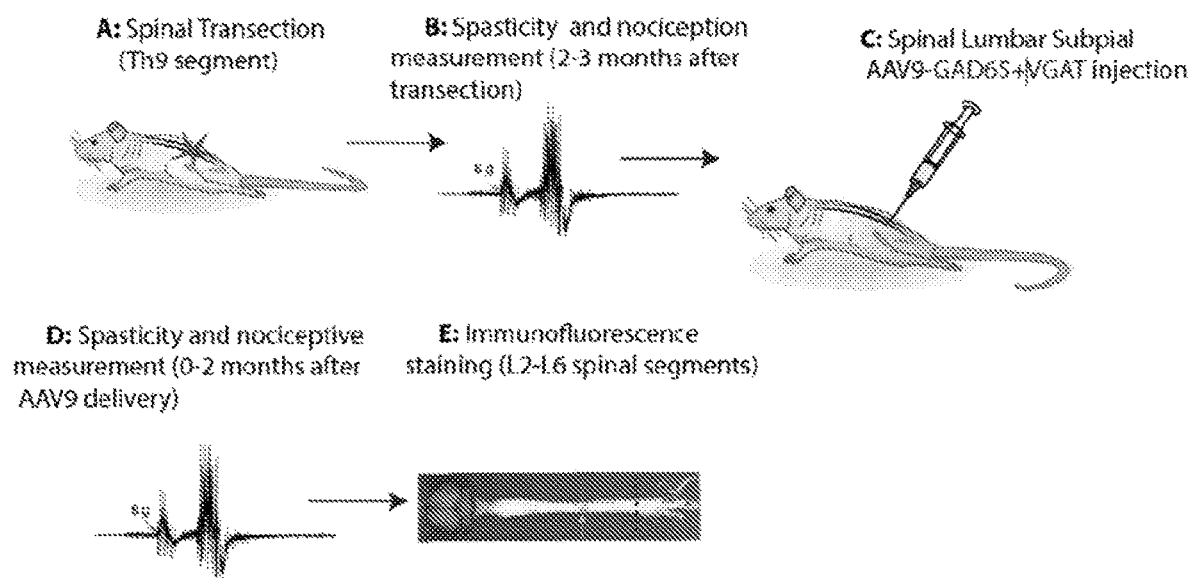
FIG. 1 is a pictorial diagram showing an exemplary methodology for performing the methods of the invention.

The present invention is based on the observation that a combined treatment composed of spinal segment-specific upregulation of GAD65 (glutamatedecarboxylase) gene and VGAT (vesicular GABA transporter) gene in rats with ischemia-induced spasticity leads to an antispasticity effect, and that such a combined treatment results in decreased muscle spacticity.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

A "therapeutic effect," as used herein, encompasses a therapeutic benefit and/or a prophylactic benefit as described herein.

As used herein, the terms "reduce" and "inhibit" are used together because it is recognized that, in some cases, a decrease can be reduced below the level of detection of a particular assay. As such, it may not always be clear whether the expression level or activity is "reduced" below a level of detection of an assay, or is completely "inhibited." Nevertheless, it will be clearly determinable, following a treatment according to the present methods.

As used herein, "treatment" or "treating" means to administer a composition to a subject or a system with an undesired condition. The condition can include a disease or disorder. "Prevention" or "preventing" means to administer a composition to a subject or a system at risk for the condition. The condition can include a predisposition to a disease or disorder. The effect of the administration of the composition to the subject (either treating and/or preventing) can be, but is not limited to, the cessation of one or more symptoms of the condition, a reduction or prevention of one or more symptoms of the condition, a reduction in the severity of the condition, the complete ablation of the condition, a stabilization or delay of the development or progression of a particular event or characteristic, or minimization of the chances that a particular event or characteristic will occur.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, a "regulatory gene" or "regulatory sequence" is a nucleic acid sequence that encodes products (e.g., transcription factors) that control the expression of other genes.

As used herein, a "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from eukaryotic mRNA, genomic DNA sequences from eukaryotic DNA, and synthetic nucleic acids. A transcription termination sequence will usually be located 3' to the coding sequence.

As used herein, a "promoter" is defined as a regulatory DNA sequence generally located upstream of a gene that mediates the initiation of transcription by directing RNA polymerase to bind to DNA and initiating RNA synthesis. A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular compound or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "functionally linked" and "operably linked" are used interchangeably and refer to a functional relationship between two or more DNA segments, in particular gene sequences to be expressed and those sequences controlling their expression. For example, a promoter/enhancer sequence, including any combination of cis-acting transcriptional control elements is operably linked to a coding sequence if it stimulates or modulates the transcription of the coding sequence in an appropriate host cell or other expression system. Promoter regulatory sequences that are operably linked to the transcribed gene sequence are physically contiguous to the transcribed sequence.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

A conservative substitution may include substitution such as basic for basic, acidic for acidic, polar for polar, etc. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput. Appl Biosci. 9: 745-756; Taylor W. R. (1986) "The classification of amino acid conservation" J. Theor. Biol. 119; 205-218). Conservative substitutions may be made, for example, according to the table below which describes a generally accepted Venn diagram grouping of amino acids.

number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the following sequence comparison algorithms or by manual alignment and visual inspection. The invention provides polypeptides that are substantially identical to the polypeptides, respectively, exemplified herein, as well as uses thereof including, but not limited to, use for treating or preventing neurological diseases or disorders, e.g., neurodegenerative diseases or disorders, and/or treating SCI. Optionally, the identity exists over a region that is at least about 50 nucleotides in length, or more preferably over a region that is 100 to 500 or 1000 or more nucleotides in length, or the entire length of the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods

TABLE 1

| Grouping of amino acids | | | |
|---|---|---|---|
| Characteristic | Set | Characteristic | Sub-set |
| Hydrophobic | F W Y H K M I L V A G C | Aromatic Aliphatic | F W Y H I L V |
| Polar | W Y H K R E D C S T N Q | Charged Positive<br>Charged Negative | H K R E D H K R<br>E D |
| Small | V C A G S P T N D | Tiny | A G S |

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Two examples of algorithms that are suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). In various embodiments, nucleic acids are isolated when purified away from other cellular components or other contaminants (e.g., other nucleic acids or proteins present in the cell) by standard techniques including, including alkaline/SDS treatment, CsCl banding, column chromatography, agarose gel electrophoresis and others well-known in the art. See e.g., F. Ausubel, et al., ed. (1987) Current Protocols in Molecular Biology, Greene Publishing and Wiley Interscience, New York. In various embodiments, a nucleic acid is, for example, DNA or RNA and may or may not contain intronic sequences. In a preferred embodiment, the nucleic acid is a cDNA molecule.

As used herein "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "neuron" include a neuron and a portion or portions thereof (e.g., the neuron cell body, an axon, or a dendrite). The term "neuron" as used herein denotes nervous system cells that include a central cell body or soma, and two types of extensions or projections: dendrites, by which, in general, the majority of neuronal signals are conveyed to the cell body, and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment or methods according to the invention include cerebellar granule neurons, dorsal root ganglion neurons, and cortical neurons.

The term "neuronal degeneration" is used broadly and refers to any pathological changes in neuronal cells, including, without limitation, death or loss of neuronal cells, any changes that precede cell death, and any reduction or loss of an activity or a function of the neuronal cells. The pathological changes may be spontaneous or may be induced by any event and include, for example, pathological changes associated with apoptosis. The neurons may be any neurons, including without limitation sensory, sympathetic, parasympathetic, or enteric, e.g., dorsal root ganglia neurons, motor neurons, and central neurons, e.g., neurons from the spinal cord. Neuronal degeneration or cell loss is a characteristic of a variety of neurological diseases or disorders, e.g., neurodegenerative diseases or disorders. In some embodiments, the neuron is a sensory neuron. In some embodiments, the neuron is a motor neuron. In some embodiments, the neuron is a damaged spinal cord neuron.

As used herein, "spasticity" refers to a condition in which certain muscles are continuously contracted. This contraction causes stiffness or tightness of the muscles and can interfere with normal movement, speech, and gait. Spasticity mostly occurs in disorders of the central nervous system (CNS) affecting the upper motor neurons in the form of a lesion, such as spastic diplegia, or upper motor neuron syndrome, and can also be present in various types of multiple sclerosis, where it occurs as a symptom of the progressively-worsening attacks on myelin sheaths and is thus unrelated to the types of spasticity present in neuromuscular cerebral palsy rooted spasticity disorders. Without being bound by theory, spasticity develops when an imbalance occurs in the excitatory and inhibitory input to a motor neurons caused by damage to the spinal cord and/or central nervous system. The damage causes a change in the balance of signals between the nervous system and the muscles, leading to increased excitability in muscles. Spasticity is found in conditions where the brain and/or spinal cord are damaged or fail to develop normally; these include cerebral palsy, multiple sclerosis, spinal cord injury, and acquired brain injury including stroke.

As used herein, "neurodegenerative disorder" or a "neurological disorder" refers to a disorder which causes morphological and/or functional abnormality of a neural cell or a population of neural cells. The neurodegenerative disorder can result in an impairment or absence of a normal neurological function or presence of an abnormal neurological function in a subject. For example, neurodegenerative disorders can be the result of disease, injury, and/or aging. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurodegeneration can occur in any area of the brain of a subject and is seen with many disorders including, for example, head trauma, stroke, ALS, multiple sclerosis, Huntington's disease, Parkinson's disease, and Alzheimer's disease.

As used herein, the term "nociception" refers to the sensory nervous system's response to certain harmful or potentially harmful stimuli. In nociception, intense chemical (e.g., chili powder in the eyes), mechanical (e.g., cutting, crushing), or thermal (heat and cold) stimulation of sensory nerve cells called nociceptors produces a signal that travels along a chain of nerve fibers via the spinal cord to the brain. Nociception triggers a variety of physiological and behavioral responses and usually results in a subjective experience of pain in sentient beings.

Gamma-aminobutyric acid (GABA) and glutamate are the primary inhibitory and excitatory neurotransmitters in mammals. The balance between GABA and glutamate controls diverse processes such as neurogenesis, movement, circadian clocks, tissue development and blood glucose regulation. GABA is synthesized from glutamate by the 65 kDa and 67 kDa isoforms of the pyridoxal phosphate (PLP) dependent enzyme Glutamic Acid Decarboxylase (GAD65 and GAD67). Human GAD65 and GAD67 have been isolated and cloned by Bu et al. (1992) Proc Natl Acad Sci 89:2115-2119. Human GAD65 cDNA encodes a Mr 65,000 polypeptide, with 585 amino acid residues (Genbank Accession No. NM000818; M81882), Human GAD67 encodes a Mr 67,000 polypeptide, with 594 amino acid residues (Genbank Accession No. NM013445; M81883); each of which is incorporated herein by reference). See also, US Pub. No. 2016/0081956, incorporated herein by reference).

Additional nucleic acid and amino acid sequences for human GAD65 are known in the art. See, for example, GenBank Accession No.: Q05329, human Glutamate decarboxylase 2 (GAD2/GAD65), which provides the amino acid sequence (SEQ ID NO: 1):

```
           10         20         30         40
    MASPGSGFWS FGSEDGSGDS ENPGTARAWC QVAQKFTGGI 50         60         70         80
    GNKLCALLYG DAEKPAESGG SQPPRAAARK AACACDQKPC 90        100        110        120
    SCSKVDVNYA FLHATDLLPA CDGERPTLAF LQDVMNILLQ 130        140        150        160
    YVVKSFDRST KVIDFHYPNE LLQEYNWELA DQPQNLEEIL 170        180        190        200
    MHCQTTLKYA IKTGHPRYFN QLSTGLDKVG LAADWLTSTA 210        220        230        240
    NTNMFTYEIA PVFVLLEYVT LKKMREIIGW PGGSGDGIFS 250        260        270        280
    PGGAISNMYA MMIARFKMFP EVKEKGMAAL PRLIAFTSEH 290        300        310        320
    SHFSLKKGAA ALGIGTDSVI LIKCDERGKM IPSDLERRIL 330        340        350        360
    EAKQKGFVPF LVSATAGTTV YGAFDPLLAV ADICKKYKIW 370        380        390        400
    MHVDAAWGGG LLMSRKHKWK LSGVERANSV TWNPHKMMGV 410        420        430        440
    PLQCSALLVR EEGLMQNCNQ MHASYLFQQD KHYDLSYDTG 450        460        470        480
    DKALQCGRHV DVFKLWLMWR AKGTTGFEAH VDKCLELAEY 490        500        510        520
    LYNIIKNREG YEMVFDGKPQ HTNVCFWYIP PSLRTLEDNE 530        540        550        560
    ERMSRLSKVA PVIKARMMEY GTTMVSYQPL GDKVNFFRKV 570        580
    ISNPAATHQD IDFLIEEIER LGQDL
```

See also, for example, GenBank Accession No.: X69936, *Homo sapiens* mRNA for glutamate decarboxylase (GAD2/GAD65), which provides the nucleic acid sequence (SEQ ID NO: 2):

```
  1    atgtcccta tacatcacca tcaccatcac ctggttccgc gtggatccga agcttcgaat 61    tctggctttt ggtctttcgg tgcggaagat ggctctgggg attccgagaa tcccggcaca 121    gcgcgagcct ggtgccaagt ggctcagaag ttcacgggcg gcatcggaaa caaactgtgc 181    gccctgctct acggagacgc cgagaagccg gcggagagcg gcgggagcca accccgcgg 241    gccgccgccc ggaaggccgc ctgcgcctgc gaccagaagc cctgcagctg ctccaaagtg 301    gatgtcaact acgcgtttct ccatgcaaca gacctgctgc cggcgtgtga tggagaaagg 361    cccactttgg cgtttctgca agatgttatg aacattttac ttcagtatgt ggtgaaaagt
```

-continued

```
 421   ttcgatagat caaccaaagt gattgatttc cattatccta atgagcttct ccaagaatat 481   aattgggaat tggcagacca accacaaaat ttggaggaaa ttttgatgca ttgccaaaca 541   actctaaaat atgcaattaa aacagggcat cctagatact tcaatcaact ttctactggt 601   ttggatatgg ttggattagc agcagactgg ctgacatcaa cagcaaatac taacatgttc 661   acctatgaaa ttgctccagt atttgtgctt ttggaatatg tcacactaaa gaaaatgaga 721   gaaatcattg gctggccagg gggctctggc gatgggatat tttctcccgg tggcgccata 781   tctaacatgt atgccatgat gatcgcacgc tttaagatgt tcccagaagt caaggagaaa 841   ggaatggctg ctcttcccag gctcattgcc ttcacgtctg aacatagtca tttttctctc 901   aagaagggag ctgcagcctt agggattgga acagacagcg tgattctgat taaatgtgat 961   gagagaggga aaatgattcc atctgatctt gaaagaagga ttcttgaagc caaacagaaa 1021   gggtttgttc ctttcctcgt gagtgccaca gctggaacca ccgtgtacgg agcatttgac 1081   cccctcttag ctgtcgctga catttgcaaa aagtataaga tctggatgca tgtggatgca 1141   gcttggggtg ggggattact gatgtcccga aaacacaagt ggaaactgag tggcgtggag 1201   agggccaact ctgtgacgtg gaatccacac aagatgatgg gagtcccttt gcagtgctct 1261   gctctcctgg ttagagaaga gggattgatg cagaattgca accaaatgca tgcctcctac 1321   ctctttcagc aagataaaca ttatgacctg tcctatgaca ctggagacaa ggccttacag 1381   tgcggacgcc acgttgatgt ttttaaacta tggctgatgt ggagggcaaa ggggactacc 1441   gggtttgaag cgcatgttga taaatgtttg gagttggcag agtatttata caacatcata 1501   aaaaaccgag aaggatatga gatggtgttt gatgggaagc ctcagcacac aaatgtctgc 1561   ttctggtaca ttcctccaag cttgcgtact ctggaagaca atgaagagag aatgagtcgc 1621   ctctcgaagg tggctccagt gattaaagcc agaatgatgg agtatggaac cacaatggtc 1681   agctaccaac ccttgggaga caaggtcaat ttcttccgca tggtcatctc aaacccagcg 1741   gcaactcacc aagacattga cttcctgatt gaagaaatag aacgccttgg acaagattta 1801   taa
```

GABA acts at inhibitory synapses in the brain by binding to specific transmembrane receptors in the plasma membrane of both pre- and postsynaptic neuronal processes. This binding causes the opening of ion channels to allow the flow of either negatively charged chloride ions into the cell or positively charged potassium ions out of the cell. This action results in a negative change in the transmembrane potential, usually causing hyperpolarization. Two general classes of GABA receptor are known: $GABA_A$ in which the receptor is part of a ligand-gated ion channel complex, and $GABA_B$ metabotropic receptors, which are G protein-coupled receptors that open or close ion channels via intermediaries (G proteins).

Loss of GABA-mediated pre-synaptic inhibition after spinal injury plays a key role in the progressive increase in spinal reflexes and the appearance of spasticity. Clinical studies show that the use of baclofen ($GABA_B$ receptor agonist), while effective in modulating spasticity is associated with major side effects such as general sedation and progressive tolerance development. The present study provides an assessment as to whether a combined therapy composed of spinal segment-specific upregulation of GAD65 (glutamate decarboxylase) gene and VGAT (vesicular GABA transporter) gene will lead to an anti spasticity effect.

VGAT (vesicular GABA transporter) (also known as vesicular inhibitory amino acid transporter (VIAAT)) is a protein that in humans is encoded by the SLC32A1 gene (also known as the VGAT gene). VGAT is highly concentrated in the nerve endings of GABAergic neurons in the brain and spinal cord but also in glycinergic nerve endings. Caudhry, et al., J. Neurosci., 18(23):9733-9750 (1998), incorporated herein by reference. Nucleic acid and amino acid sequences for human VGAT are known in the art. See, for example, GenBank Accession No.: Q9H598, human Vesicular inhibitory amino acid transporter (VIAAT/VGAT), which provides the amino acid sequence (SEQ ID NO: 3):

```
           10         20         30         40
    MATLLRSKLS NVATSVSNKS QAKMSGMFAR MGFQAATDEE 50         60         70         80
    AVGFAHCDDL DFEHRQGLQM DILKAEGEPC GDEGAEAPVE 90        100        110        120
    GDIHYQRGSG APLPPSGSKD QVGGGGEFGG HDKPKITAWE 130        140        150        160
    AGWNVTNAIQ GMFVLGLPYA ILHGGYLGLF LIIFAAVVCC 170        180        190        200
    YTGKILIACL YEENEDGEVV RVRDSYVAIA NACCAPRFPT
```

```
         210        220        230        240
  LGGRVVNVAQ IIELVMTCIL YVVVSGNLMY NSFPGLPVSQ 250        260        270        280
  KSWSIIATAV LLPCAFLKNL KAVSKFSLLC TLAHFVINIL 290        300        310        320
  VIAYCLSRAR DWAWEKVKFY IDVKKFPISI GIIVFSYTSQ 330        340        350        360
  IFLPSLEGNM QQPSEFHCMM NWTHIAACVL KGLFALVAYL 370        380        390        400
  TWADETKEVI TDNLPGSIRA VVNIFLVAKA LLSYPLPFFA 410        420        430        440
  AVEVLEKSLF QEGSRAFFPA CYSGDGRLKS WGLTLRCALV 450        460        470        480
  VFTLLMAIYV PHFALLMGLT GSLTGAGLCF LLPSLFHLRL 490        500        510        520
  LWRKLLWHQV FFDVAIFVIG GICSVSGFVH SLEGLIEAYR

TNAED
```

See also, for example, GenBank Accession No.: NM_080552, *Homo sapiens* solute carrier family 32 member 1 (SLC32A1), mRNA, which provides the nucleic acid sequence (SEQ ID NO: 4):

```
   1 gctcgcgccc cgcggcagct ccgcagtgca ctagccacca ccgccgccgc cgccgctccg
  61 ccagacctgc tgccagcttg cccggtccag ccctgagaga gcctcgaacg ccagctgcga
 121 gggtcatgag ccacagagcc ccggggcgcc gcgcggagag caagcggaga tagcgacttt
 181 gcgccccca gccctcgcct tcttgcatcg cgttcccgc atcctcgggt ccttctgtcc
 241 tttccgctgt ccccaccgcc gccatggcca ccttgctccg cagcaagctg tccaacgtgg
 301 ccacgtccgt gtccaacaag tcccaggcca agatgagcgg catgttcgcc aggatgggtt
 361 ttcaggcggc cacggatgag gaggcgctgg gcttcgcgca ttgcgacgac ctcgactttg
 421 agcaccgcca gggcctgcag atggacatcc tgaaagccga gggagagccc tgcggggacg
 481 agggcgctga agcgcccgtc gagggagaca tccattatca gcgaggcagc ggagctcctc
 541 tgccgccctc cggctccaag gaccaggtgg gaggtggtgg cgaattcggg ggccacgaca
 601 agcccaaaat cacggcgtgg gaggcaggct ggaacgtgac caacgccatc cagggcatgt
 661 tcgtgctggg cctaccctac gccatcctgc acggcggcta cctggggttg tttctcatca
 721 tccttgccgc cgttgtgtgc tgctacaccg gcaagatcct catcgcgtgc ctgtacgagg
 781 agaatgaaga cggcgaggtg gtgcgcgtgc gggactcgta cgtggccata gccaacgcct
 841 gctgcgcccc gcgcttccca acgctggggc gccgagtggt gaacgtagcg cagatcatcg
 901 agctggtgat gacgtgcatc ctgtacgtgg tggtgagtgg caacctcatg tacaacagct
 961 tcccggggct gccccgtgtcg cagaagtcct ggtccattat cgccacggcc gtgctgctgc
1021 cttgcgcctt ccttaagaac ctcaaggccg tgtccaagtt cagtctgctg tgcactctgg
1081 cccacttcgt catcaatatc ctggtcatag cctactgtct atcgcgggcg cgcgactggg
1141 cctgggagaa ggtcaagttc tacatcgacg tcaagaagtt ccccatctcc attggcatca
1201 tcgtgttcag ctacacgtct cagatcttcc tgccttcgct ggagggcaat atgcagcagc
1261 ccagcgagtt ccactgcatg atgaactgga cgcacatcgc agcctgcgtg ctcaagggcc
1321 tccttgcgct cgtcgcctac ctcacctggg ccgacgagac caaggaggtc atcacggata
1381 acctgcccgg ctccatccgc gccgtggtca catctttct ggtggccaag gcgctgttgt
1441 cctatcctct gccattcttt gccgctgtcg aggtgctgga gaagtcgctc ttccaggaag
1501 gcagccgcgc cttttttcccg gcctgctaca gcggcgacgg gcgcctgaag tcctggggggc
1561 tgacgctgcg ctgcgcgctc gtcgtcttca cgctgctcat ggccatttat gtgccgcact
1621 tcgcgctgct catgggcctc accggcagcc tcacgggcgc cggcctctgt ttcttgctgc
1681 ccagcctctt tcacctgcgc ctgctctggc gcaagctgct gtggcaccaa gtcttcttcg
1741 acgtcgccat cttcgtcatc ggcggcatct gcagcgtgtc cggcttcgtg cactccctcg
1801 agggcctcat cgaagcctac cgaaccaacg cggaggacta gggcgcaagg gcgagccccc
```

```
-continued
1861   gccgcgcttC tgcgctctct cccttctccc ctcaccccgc ccccaccagc ccagtgcgcc 1921   ctgccgccgc gcttgggagg ccaagcttta aacatctctg gttcctagtt tctgattatt 1981   cgggatggg ggggatggga ggggacaggg attcacgatc catcgcgtct gcgtttctgt 2041   tgtcctttct tttccacaac accctggttt tgggggagg cggggtgcat ttgcgggcag 2101   ggttctctgt ccttccaagt ggggcccga cactttggtt ccagtcatcg agggggttgg 2161   gaagggaggg agagggggcg cagctcgcag gcgtggcaac ttgaccttgg gggaatattt 2221   cacatccatc cagagctcgg aatctacagc gtccagccat ttccagcaag agcgcttccc 2281   attccggaga cgtttcaacc ctgcagcggg aaaggctgac tgggaaatcc attttgggtg 2341   ggcaatttcc ttcaacgaag ccggaaggcg agaagccgcg gcggggccag cttgcctgcc 2401   ggttttcagg aatctaaact ctcatcttgt gcaatttatc aggtgtggaa ctgttctact 2461   gtgcgtgtgg tgtgctcgtg gtgaataaga tgaaatgtat atcagaaaaa aatctatctc 2521   taatttagag tgcggtacat aattatatcc gcaaataaag aagagacaaa ggctaaaaaa 2581   a
```

Accordingly, in one aspect, the invention provides a vector comprising a nucleotide sequence encoding GAD65 and VGAT. Also within the scope of the invention is a polypeptide encoded by nucleotide sequence that has at least 60% homology to GAD65 or a functional fragment thereof. A polypeptide encoded by nucleotide sequence that about 70% homology, about 75% homology, about 80% homology, about 85% homology, about 90% homology, about 95% homology, about 99% homology to GAD65 or a fragment thereof. Also within the scope of the invention is a polypeptide encoded by nucleotide sequence that has at least 60% homology to VGAT or a fragment thereof. A polypeptide encoded by nucleotide sequence that about 70% homology, about 75% homology, about 80% homology, about 85% homology, about 90% homology, about 95% homology, about 99% homology to VGAT or a fragment thereof.

Decreased or completely lost activity of a facilitatory supraspinal input into spinal GABA-ergic inhibitory interneurons and resulting decrease in local segmental inhibition has been postulated as one of the key mechanisms leading to the development of muscle spasticity in patients with spinal cord injury (SCI). Comparably, loss of spinal inhibitory interneurons, as seen after transient episodes of spinal cord ischemia leads to development of functionally defined muscle spasticity and rigidity. Independent of the insult nature (e.g., spinal trauma or ischemia), clinical and experimental animal pharmacology studies have shown a comparable and potent antispasticity effect after systemic or spinal treatment with most commonly used antispasticity agent baclofen (GABA$_B$ receptor agonist). The primary site of baclofen-mediated hyperpolarizing action is believed to be at presynaptic Ia afferents.

One of the major limitations of systemic baclofen treatment, however, is the lack of a localized spinal segment-restricted effect and relatively high doses required to achieve clinically relevant relief of spasticity frequently produce unwanted systemic side effects such as sedation. Direct spinal delivery of baclofen using chronic intrathecal catheter provides a more site-restricted effect with less pronounced systemic activity, however it requires surgical intervention and ensuing complications associated with chronic intrathecal catheterization such as cerebrospinal fluid leak or infection has been described. More importantly, limits of effective long-term use of IT baclofen include the development of baclofen tolerance (i.e., progressive escalation of dose to achieve consistent anti-spasticity effect) and withdrawal after an abrupt termination of baclofen treatment.

Preferential expression of GAD65 gene in infected astrocytes (as opposed to neurons) appears to provide a specific advantage with respect to expected GABA mediated anti-spasticity effect (see, e.g., WO2014/116652, incorporated herein by reference). As has been shown in vitro, infection of primary astrocytes led to a $Ca^{2+}$ independent increase in extracellular GABA concentration. Accordingly, it is expected that astrocyte-mediated GABA release in the spinal parenchyma will be independent of the functionality and connectivity of local neuronal inhibitory circuitry and will specifically exert its hyperpolarizing effect on $GABA_B$ receptor expressed on Ia afferents and/or α-motoneurons. The biological activity of astrocyte-produced GABA was confirmed by its depolarization-inducing effect on preferentially $GABA_A$ receptor-expressing cultured hNT neurons.

The use of a dual GAD65 and VGAT gene therapy represents a novel approach previously not tested in the context of spinal or brain delivery with the goal to increase regional neuronal inhibition. The core of this discovery is that both genes need to be upregulated in order to achieve a functionally relevant inhibition of otherwise hyperexcitable neurons. The potency of this treatment effect indicates that sufficient quantities of releasable GABA is available in the synaptic cleft to induce inhibition of postsynaptic membrane, leading to a decrease in α-motoneuron excitability and resulting suppression of muscle spasticity.

Accordingly, in another aspect, the invention provides a method of treating spasticity in a subject by spinal-specific upregulation of the GAD65 gene and VGAT gene. In various embodiments, upregulation of GAD65 and VGAT includes administering a viral vector encoding GAD65 and VGAT, and expressing the GAD65 and VGAT in the spinal cord of the subject, thereby decreasing spasticity in the subject.

Viral vectors can be particularly useful for introducing a polynucleotide useful in performing a method of the invention into a target cell. Viral vectors have been developed for use in particular host systems, particularly mammalian systems, and include, for example, retroviral vectors, other lentivirus vectors such as those based on the human immunodeficiency virus (HIV), adenovirus vectors (AV), adeno-associated virus vectors (AAV), herpes virus vectors, vaccinia virus vectors, and the like (see Miller and Rosman, *BioTechniques* 7:980-990, 1992; Anderson et al., *Nature* 392:25-30 *Suppl.*, 1998; Verma and Somia, *Nature* 389:239-242, 1997; Wilson, *New Engl. J. Med.* 334:1185-1187 (1996), each of which is incorporated herein by reference). In one aspect of the invention, a lentivirus, an AV, or an AAV is utilized. Adenoviruses represent the largest nonenveloped viruses, because they are the maximum size able to be transported through the endosome (i.e., envelope fusion is not necessary). The virion also has a unique "spike" or fibre associated with each penton base of the capsid that aids in attachment to the host cell. AAV is a dependent parvovirus that by definition requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells.

Once in the nucleus, the virus uncoats and the transgene is expressed from a number of different forms—the most persistent of which are circular monomers. AAV will integrate into the genome of 1-5% of cells that are stably transduced (Nakai et al., *J. Virol.* 76: 11343-349, 2002). Expression of the transgene can be exceptionally stable. Because progeny virus is not produced from AAV infection in the absence of helper virus, the extent of transduction is restricted only to the initial cells that are infected with the virus. It is this feature which makes AAV a suitable gene therapy vector for the present invention.

Additional references describing adenovirus vectors and other viral vectors which could be used in the methods of the present invention include the following: Horwitz, M. S., Adenoviridae and Their Replication, in Fields, B., et al. (eds.) *Virology*, Vol. 2, Raven Press New York, pp. 1679-1721, 1990); Graham, F., et al., pp. 109-128 in *Methods in Molecular Biology*, Vol. 7: Gene Transfer and Expression Protocols, Murray, E. (ed.), Humana Press, Clifton, N.J. (1991); Miller, N., et al., FASEB Journal 9: 190-199, 1995; Schreier, H, *Pharmaceutica Acta Helvetiae* 68: 145-159, 1994; Schneider and French, Circulation 88:1937-1942, 1993; Curiel D. T., et al., *Human Gene Therapy* 3: 147-154, 1992; Graham, F. L., et al., WO 95/00655 (5 Jan. 1995); Falck-Pedersen, E. S., WO 95/16772 (22 Jun. 1995); Denefle, P. et al., WO 95/23867 (8 Sep. 1995); Haddada, H. et al., WO 94/26914 (24 Nov. 1994); Perricaudet, M. et al., WO 95/02697 (26 Jan. 1995); Zhang, W., et al., WO 95/25071 (12 Oct. 1995). A variety of adenovirus plasmids are also available from commercial sources, including, e.g., Microbix Biosystems of Toronto, Ontario (see, e.g., Microbix Product Information Sheet: Plasmids for Adenovirus Vector Construction, 1996).

Additional references describing AAV vectors which could be used in the methods of the present invention include the following: Carter, B., *Handbook of Parvoviruses*, vol. I, pp. 169-228, 1990; Berns, *Virology*, pp. 1743-1764 (Raven Press 1990); Carter, B., *Curr. Opin. Biotechnol.*, 3: 533-539, 1992; Muzyczka, N., *Current Topics in Microbiology and Immunology*, 158: 92-129, 1992; Flotte, T. R., et al., *Am. J. Respir. Cell Mol. Biol.* 7:349-356, 1992; Chatterjee et al., *Ann. NY Acad. Sci.*, 770: 79-90, 1995; Flotte, T. R., et al., WO 95/13365 (18 May 1995); Trempe, J. P., et al., WO 95/13392 (18 May 1995); Kotin, R., *Human Gene Therapy*, 5: 793-801, 1994; Flotte, T. R., et al., *Gene Therapy* 2:357-362, 1995; Allen, J. M., WO 96/17947 (13 Jun. 1996); and Du et al., *Gene Therapy* 3: 254-261, 1996.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, ovine AAV, and any other AAV now known. In one embodiment, the AAV is AAV type 2. In another embodiment, the AAV is AAV type 9.

Depending on the host cell/vector system utilized, any of a number of suitable transcription and translation elements, including constitutive and inducible promoters, transcription enhancer elements, transcription terminators, and the like can be used in the expression vector (Bitter et al., *Meth. Enzymol.* 153:516-544, 1987). As defined above, reference to a "promoter" or "promoter sequence" is to be taken in its broadest context and includes a DNA regulatory region capable of binding RNA polymerase in a cell and initiating transcription of a polynucleotide or polypeptide coding sequence such as messenger RNA, ribosomal RNAs, small nuclear of nucleolar RNAs or any kind of RNA transcribed by any class of any RNA polymerase. "Promoters" contemplated herein may also include the transcriptional regulatory sequences of a classical genomic gene, including the Goldberg-Hogness box which is required for accurate transcription initiation in eukaryotic cells, with or without a CAT box sequence and additional regulatory elements (i.e., upstream activating sequences, enhancers and silencers).

Placing a sequence under the regulatory control of a promoter sequence means positioning said molecule such that expression is controlled by the promoter sequence. Promoters are generally positioned 5' (upstream) to the genes that they control. In the construction of heterologous promoter/structural gene combinations, generally promoter position may be a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the positioning of a regulatory sequence element with respect to a heterologous gene to be placed under its control is defined by the positioning of the element in its natural setting, i.e., the genes from which it is derived. Again, as is known in the art, some variation in this distance can also occur.

Exemplary promoters useful in the methods and treatment regimens of the present invention include, but are not limited to, human ubiquitin promoter and human synapsin promoter. However, other known tissue-specific or cell-specific promoters may be used.

Suitable host cells for producing recombinant AAV particles include, but are not limited to, microorganisms, yeast cells, insect cells, and mammalian cells, that can be, or have been, used as recipients of a exogenous nucleic acid molecule. Thus, a "host cell" as used herein generally refers to a cell which has been transfected with an exogenous nucleic acid molecule. The host cell includes any eukaryotic cell or cell line so long as the cell or cell line is not incompatible with the protein to be expressed, the selection system chosen or the fermentation system employed.

The AAV vectors can be formulated into preparations for injection or administration by dissolving, suspending or emulsifying them in appropriate, pharmaceutically acceptable carriers or diluents. Examples of such pharmaceutically acceptable carriers or diluents include an aqueous or non-aqueous solvent, such as oils, synthetic aliphatic acid glycerides, esters of higher aliphatic acids or propylene glycol;

and if desired, with conventional additives such as solubilizers, isotonic agents, suspending agents, emulsifying agents, stabilizers and preservatives.

If a viral vector specific for the cell type is not available, the vector can be modified to express a receptor (or ligand) specific for a ligand (or receptor) expressed on the target cell, or can be encapsulated within a liposome, which also can be modified to include such a ligand (or receptor). A peptide agent can be introduced into a cell by various methods, including, for example, by engineering the peptide to contain a protein transduction domain such as the human immunodeficiency virus TAT protein transduction domain, which can facilitate translocation of the peptide into the cell. In addition, there are a variety of biomaterial-based technologies such as nano-cages and pharmacological delivery wafers (such as used in brain cancer chemotherapeutics) which may also be modified to accommodate this technology.

In addition to cell integrating gene transfer after the use of lentiviral vectors, there are reports of successful GAD65 gene overexpression after AAV-GAD65 injections into subthalamic nuclei. In those studies, persistent GAD65 expression was seen up to 4-5 months after AAV-GAD65 injections. More importantly, recent systematic data demonstrate a high efficiency of AAV-based gene delivery into rat or minipig striatum even after a limited number of AAV injections (1-2 injections). Thus, in another embodiment, the present invention employs an AAV-based, genome-non-integrating GAD65-encoding and VGAT-encoding vector to achieve segment-specific GAD65 and VGAT expression.

By combining spinal delivery of GAD65 and VGAT, a significant and functionally relevant increase in spinal spasticity inhibition was achieved. The potency of spinal inhibition was tested in a well-characterized model of spinal trauma-induced muscle spasticity in rat. This animal model is characterized by the presence of highly developed spinal hyperreflexia and resulting muscle spasticity clearly present at chronic stages after spinal injury. Chronic spastic animals which received spinal subpial injection of GAD65+VGAT (delivered in AAV9-UBI vector) showed a significant suppression of spasticity response seen at 5 weeks after gene delivery and this significant treatment effect continue for at least the 8-th week. Immunofluoresence analysis showed the appearance of a mixed inhibitory-excitatory neurotransmitter phenotype in spinal interneurons as evidenced by colocalization of GAD65 and VGAT expression with glutamatergic markers VGLUT1 and VGLUT2. In animals injected with control GFP vector no anti-spasticity effect was seen and no co-localization of GAD65 and VGAT expression with glutamatergic markers VGLUT1 and VGLUT2 was detected.

Administering the instant combinational therapy can be effected or performed using any of the various methods and delivery systems known to those skilled in the art. As used herein, the term "administration" or "administering" is defined to include an act of providing a compound or pharmaceutical composition of the invention to a subject in performing the methods of the invention. Exemplary routes of administration include, but are not limited to, intravenously, intraarticularly, intracisternally, intraocularly, intraventricularly, intrathecally, subpially, intramuscularly, intraperitoneally, intradermally, intracavitarily, and the like, as well as combinations of any two or more thereof. In certain embodiments, the AAV may be delivered directly into the spinal parenchyma, intrathecal space of the spine, into the spinal subpial space of the subject, and/or into the peripheral spastic muscle to achieve spinal upregulation of the GAD65 gene and VGAT gene. See, e.g., WO2016/122791, incorporated herein by reference.

The term "therapeutically effective amount" or "effective amount" means the amount of the compound or composition that will elicit the biological or medical response of a tissue, system, animal or human that is being sought by the researcher, veterinarian, medical doctor or other clinician, e.g., spinal upregulation of the GAD65 gene and VGAT gene. Thus, the term "therapeutically effective amount" is used herein to denote any amount of a formulation that causes a substantial improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation. For example, a "therapeutically effective amount" of, e.g., an AAV encoding the GAD65 gene and VGAT gene or a composition comprising the AAV encoding the GAD65 gene and VGAT gene, with respect to the subject method of treatment, refers to an amount of the AAV in a preparation which, when applied as part of a desired treatment regimen brings about upregulation of the GAD65 gene and VGAT gene.

Determining a therapeutically or prophylactically effective amount of the delivery vector can be done based on animal data using routine computational methods. Appropriate doses will depend, among other factors, on the specifics of the transfer vector chosen, on the route of administration, on the mammal being treated (e.g., human or non-human primate or other mammal), age, weight, and general condition of the subject to be treated, the severity of the disorder being treated, the location of the area within the heart being treated and the mode of administration. Thus, the appropriate dosage may vary from patient to patient. An appropriate effective amount can be readily determined by one of skill in the art.

Dosage treatment may be a single dose schedule or a multiple dose schedule. Moreover, the subject may be administered as many doses as appropriate. One of skill in the art can readily determine an appropriate number of doses. However, the dosage may need to be adjusted to take into consideration an alternative route of administration, or balance the therapeutic benefit against any side effects. Such dosages may vary depending upon the therapeutic application for which the recombinant vector is employed.

Optionally, AAV-mediated delivery according to the invention may be combined with delivery by other viral and non-viral vectors. Such other viral vectors including, without limitation, adenoviral vectors, retroviral vectors, lentiviral vectors. herpes simplex virus (HSV) vectors, and baculovirus vectors may be readily selected and generated according to methods known in the art. Similarly, non-viral vectors, including, without limitation, liposomes, lipid-based vectors, polyplex vectors, molecular conjugates, polyamines and polycation vectors, may be readily selected and generated according to methods known in the art. When administered by these alternative routes, the dosage is desirable in the range described above.

In another aspect, the invention also provides a treatment regimen for treating a subject having a spinal cord injury. The treatment regimen includes administering a spinal-specific upregulation of the GAD65 gene and VGAT gene. As discussed in detail above, upregulation of GAD65 and VGAT may include administering a viral vector encoding GAD65 and VGAT, wherein GAD65 and VGAT is expressed and treats the spinal cord injury.

In addition, the methods of the invention can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine, Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexiline), and Metronidazole.

The methods of the invention can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, e.g., stroke or intracranial hemorrhage (such as cerebral hemorrhage). Likewise, the methods of the invention can be used in the treatment of chronic pain/nociception caused by such trauma.

The following examples are intended to illustrate but not limit the invention.

Example 1

Figure 2:
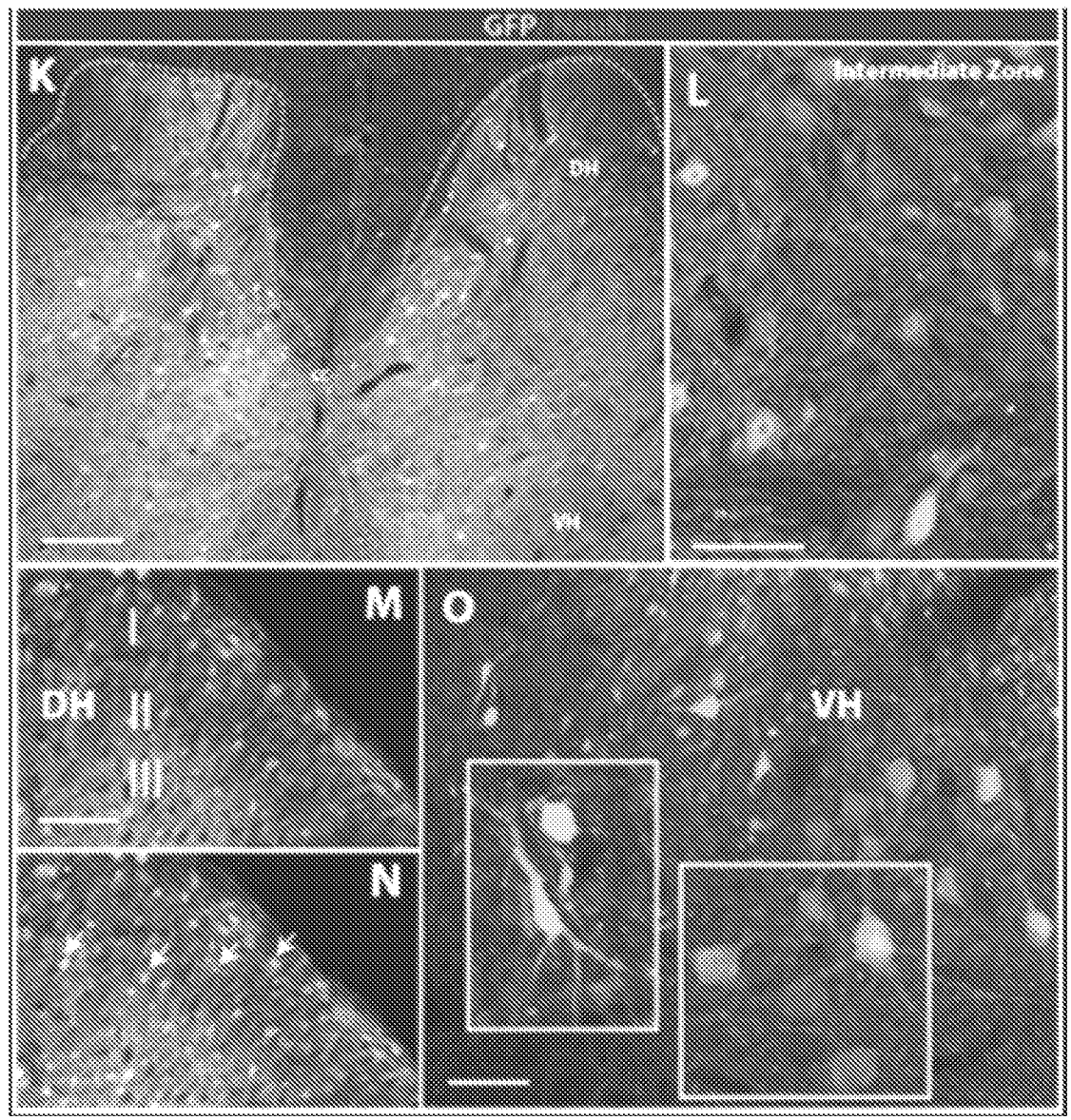
FIG. 2 is a pictorial diagram showing the distribution of transgene expression achieved after lumbar subpial AAV9-UBI-GFP delivery. A wide-spread GFP expression in interneurons through the gray matter can be seen. AAV9 virus encoding GAD65 (gutamate-decarboxylase 65) and VGAT (vesicular GABA transporter) is injected into targeted segments using subpial delivery method.

AAV9 virus encoding GAD65 (glutamate-decarboxylase 65) and VGAT (vesicular GABA transporter) is injected into targeted segments using subpial delivery method (FIG. 1). Animals (rats) with spinal injury-induced muscle spasticity were used. The distribution of transgene expression achieved after lumbar subpial AAV9-UBI-GFP delivery is shown in FIG. 2. A wide-spread GFP expression in interneurons through the gray matter can be seen.

Figures 3A, 3B:
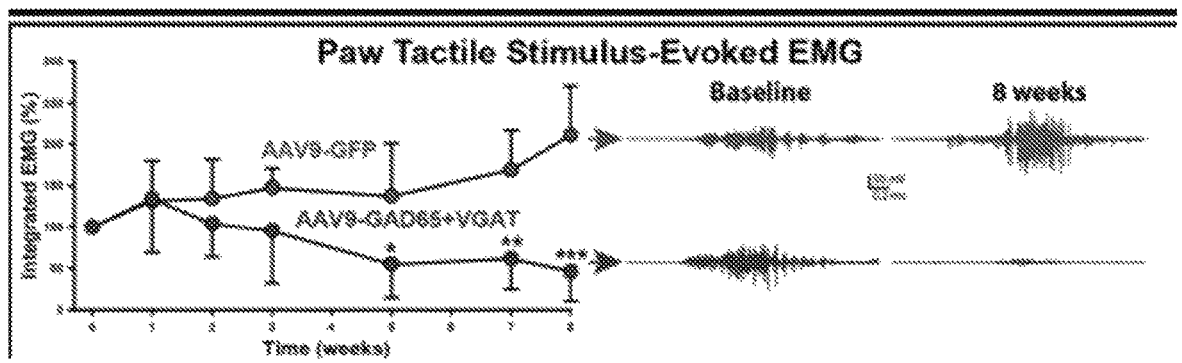
FIGS. 3A-3D are graphical diagrams showing potent anti-spasticity and anti-nociceptive effect after lumbar subpial AAV9-UBI-GAD65+VGAT delivery in chronic spinal transection-induced spastic rat.
Figures 3C, 3D:
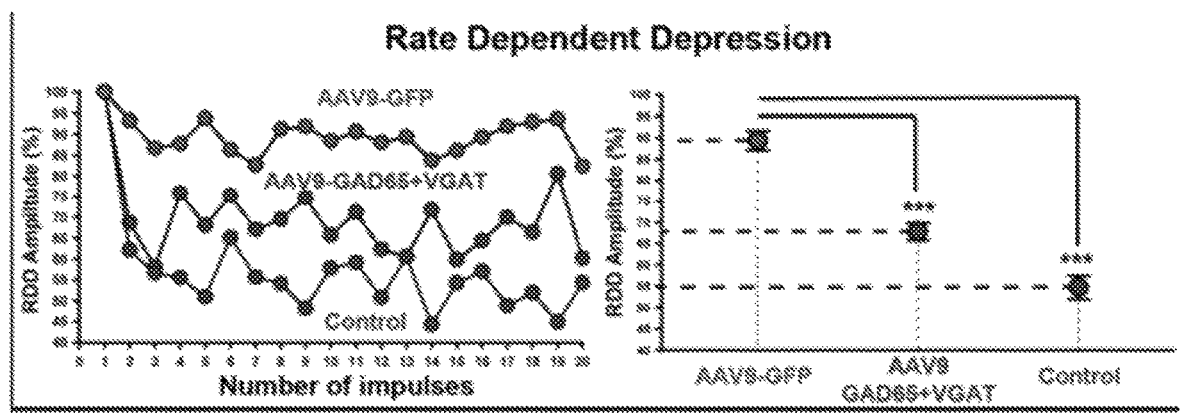

After GAD65 and VGAT gene delivery spasticity response was measured for up to 8 weeks after gene delivery. In control spastic animals a control AAV9-UBI-GFP was used. FIGS. 3A-3D show a progressive decrease in spasticity response in animals injected with AAV9-UBI-GAD65+VGAT. A significant anti-spasticity effect continue for minimum of 8 weeks after gene delivery (FIGS. 3A and 3B). Measurement of rate-dependent depression (represents an index of alert spinal inhibition) show a significant recovery if compared to control AAV9-injected animals (FIG. 3C).

Figures 4A, 4C:
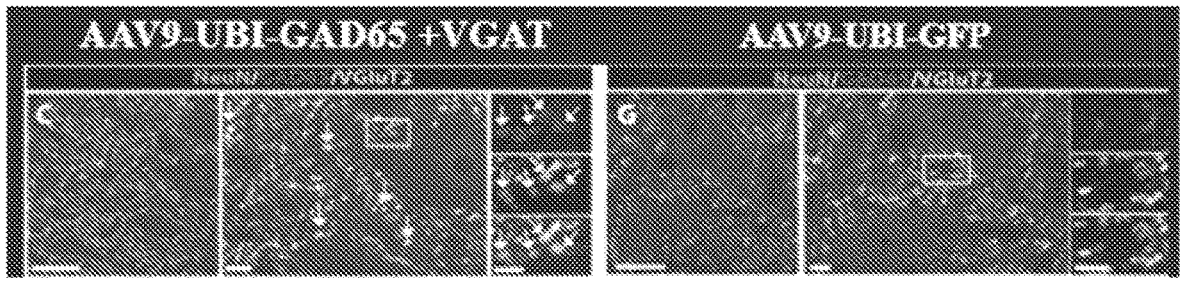
FIGS. 4A-4D are pictorial diagrams showing induction of a mixed inhibitory-excitatory neurotransmitter phenotype in spinal excitatory interneurons by lumbar subpial AAV9-UBI-GAD65+VGAT delivery. At 8 weeks immunofluorescence analysis of GAD65/VGAT gene-injected segments showed a significant upregulation of both genes and appearance of mixed inhibitory/excitatory neurotransmitter phenotype (coexpression of GAD65 or VGAT with VGLUT2 (vesicular glutamate transporter), (FIGS. 4A and 4B). No coexpression in animals injected with control AAV9 was seen (FIGS. 4C and 4D). These data confirmed an effective induction of inhibitory drive in GAD65/VGAT over-expressing neurons which likely mediate decrease in muscle spasticity.
Figures 4B, 4D:
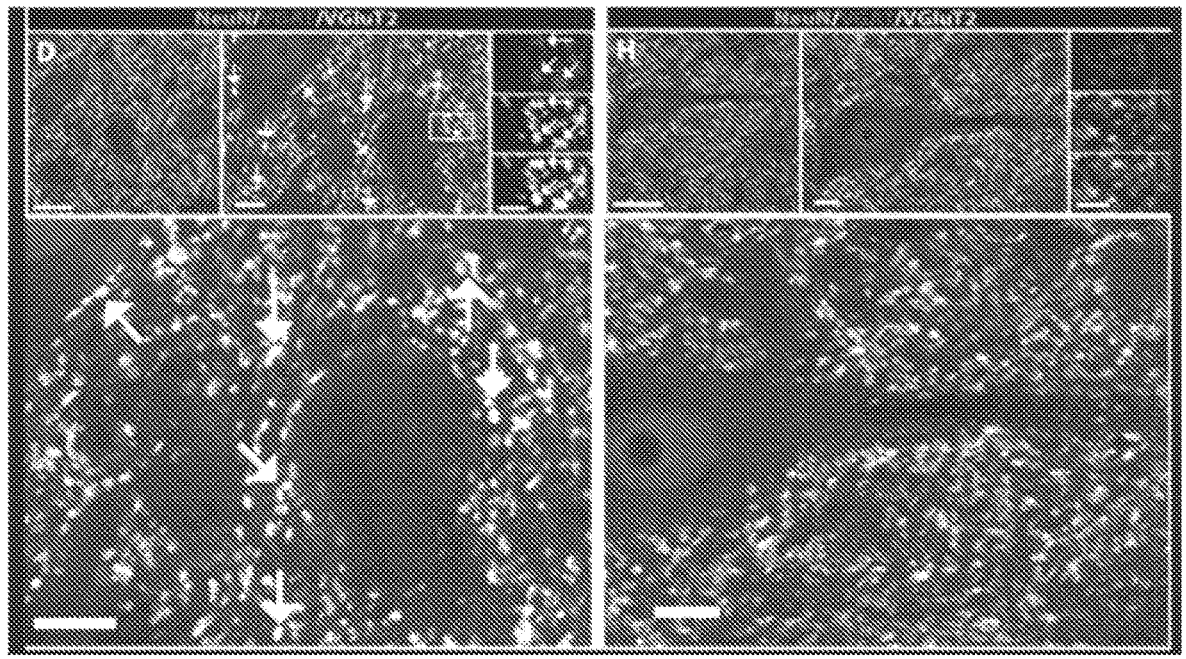
Figure 5:
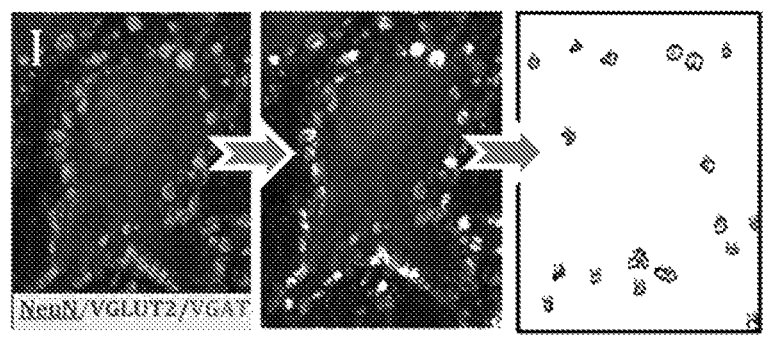
FIG. 5 is a pictorial diagram showing a significant increase in number of a mixed inhibitory-excitatory interneurons and projecting DRG neurons in lumbar spinal cord in spastic rats after lumbar subpial AAV9-UBI-GAD65+VGAT delivery. The table shows quantitative analysis of GAD65 and VGAT expression.

At 8 weeks immunofluorescence analysis of GAD65/VGAT gene-injected segments showed a significant upregulation of both genes and appearance of mixed inhibitory/excitatory neurotransmitter phenotype (co-expression of GAD65 or VGAT with VGLUT2 (vesicular glutamate transporter), (FIGS. 4A and 4B). No co-expression in animals injected with control AAV9 was seen (FIGS. 4C and 4D). These data confirmed an effective induction of inhibitory drive in GAD65/VGAT over-expressing neurons which likely mediate decrease in muscle spasticity.

Although the invention has been described with reference to the above example, it will be understood that modifications and variations are encompassed within the spirit and scope of the invention. Accordingly, the invention is limited only by the following claims.

What is claimed is:

1. A method of treating spasticity in a subject comprising administering to a subject in need thereof a therapeutically effective amount of a vector comprising a polynucleotide encoding glutamate decarboxylase (GAD65) and vesicular GABA transporter (VGAT), wherein:
    the vector is administered directly into the subpial space of the subject, GAD65 and VGAT are expressed and upregulated, and
    the expression and upregulation of GAD65 and VGAT generate spinal interneurons with a mixed inhibitory-excitatory neurotransmitter phenotype, thereby treating spasticity in the subject.

2. The method of claim 1, wherein the GAD65 and VGAT are overexpressed.

3. The method of claim 1, wherein the vector is a lentiviral vector, an AV, an AAV, or a recombinant AAV.

4. The method of claim 3, wherein the vector is a lentiviral vector.

5. The method of claim 3, wherein the vector is an AAV.

6. The method of claim 5, wherein the AAV is AAV9.

7. The method of claim 1, further comprising directly administering the vector into the spinal parenchyma of the subject, into the intrathecal space of the subject, or into a peripheral spastic muscle of the subject.

8. The method of claim 3, wherein the vector is a recombinant AAV9 comprising a GA65 polynucleotide and a VGAT polynucleotide.

9. The method of claim 8, wherein the recombinant AAV9 is AAV9-UBI-GAD65+VGAT.

10. A method for treating a subject having a spinal cord injury comprising administering a vector comprising a polynucleotide encoding glutamate decarboxylase (GAD65) and vesicular GABA transporter (VGAT), wherein:
    the vector is administered directly into the subpial space of the subject, GAD65 and VGAT are expressed and upregulated, and
    the expression and upregulation of GAD65 and VGAT generate spinal interneurons with a mixed inhibitory-excitatory neurotransmitter phenotype, thereby treating the spinal cord injury.

11. The method of claim 10, wherein the GAD65 and VGAT are overexpressed.

12. The method of claim 10, wherein the vector is a lentiviral vector, an AV, an AAV, or a recombinant AAV.

13. The method of claim 12, wherein the vector is a lentiviral vector.

14. The method of claim 12, wherein the vector is an AAV.

15. The method of claim 14, wherein the AAV is AAV9.

16. The method of claim 10, further comprising directly administering the vector into the spinal parenchyma of the subject, into the intrathecal space of the subject, or into a peripheral spastic muscle of the subject.

17. A vector comprising a promoter functionally linked to a polynucleotide encoding GAD65 and VGAT to express and upregulate GAD65 and VGAT, wherein:
    the vector is administered directly into the subpial space of the subject,
    the expression and upregulation of GAD65 and VGAT generate spinal interneurons with a mixed inhibitory-excitatory neurotransmitter phenotype, and
    the vector is used in a method of treating spasticity or a treatment regimen for treating a subject having a spinal cord injury.

18. The vector of claim 17, wherein the vector is a viral vector selected from the group consisting of a lentiviral, adenoviral, and AAV vector.

19. The vector of claim 18, wherein the vector is AAV9-UBI-GAD65+VGAT.

20. An isolated mammalian host cell containing the vector according to claim 17.

* * * * *